(12) United States Patent
Geistlich

(10) Patent No.: US 9,034,315 B2
(45) Date of Patent: May 19, 2015

(54) CELL-CHARGED MULTI-LAYER COLLAGEN MEMBRANE

(75) Inventor: Peter Geistlich, Stansstad (CH)

(73) Assignee: ED. GEISTLICH SOEHNE AG FUER CHEMISCHE INDUSTRIE, Wolhusen (CH)

( * ) Notice: Subject to any disclaimer, the term of this patent is extended or adjusted under 35 U.S.C. 154(b) by 1099 days.

(21) Appl. No.: 11/509,826

(22) Filed: Aug. 25, 2006

(65) Prior Publication Data

US 2007/0031388 A1 Feb. 8, 2007

Related U.S. Application Data

(63) Continuation-in-part of application No. 11/317,247, filed on Dec. 27, 2005, which is a continuation-in-part of application No. 10/367,979, filed on Feb. 19, 2003, now abandoned, which is a continuation-in-part of (Continued)

(30) Foreign Application Priority Data

Oct. 10, 1997 (GB) .................................... 9721585.9

(51) Int. Cl.
| | |
|---|---|
| *A61L 27/24* | (2006.01) |
| *C12N 5/077* | (2010.01) |
| *A61L 27/38* | (2006.01) |
| *A61L 15/32* | (2006.01) |
| *A61L 15/40* | (2006.01) |
| *A61L 31/00* | (2006.01) |

(Continued)

(52) U.S. Cl.
CPC ............ *C12N 5/0654* (2013.01); *A61L 27/3821* (2013.01); *A61K 35/12* (2013.01); *A61L 15/325* (2013.01); *A61L 15/40* (2013.01); *A61L 27/24* (2013.01); *A61L 27/3804* (2013.01); *A61L 27/3847* (2013.01); *A61L 31/005* (2013.01); *A61L 31/044* (2013.01); *C12N 2533/54* (2013.01)

(58) Field of Classification Search
None
See application file for complete search history.

(56) References Cited

U.S. PATENT DOCUMENTS

| 4,394,370 A | 7/1983 | Jefferies |
| 4,516,276 A | 5/1985 | Mittelmeier et al. |

(Continued)

FOREIGN PATENT DOCUMENTS

| AU | 660045 | 6/1995 |
| AU | 663150 | 9/1995 |

(Continued)

OTHER PUBLICATIONS

Mason, JM, et al., Viral vector laboratory, NSUH, Manhasset, NY, (CORR, Nov. 2000), 7 pages.

(Continued)

*Primary Examiner* — Allison Fox
(74) *Attorney, Agent, or Firm* — Rothwell, Figg, Ernst & Manbeck, P.C.

(57) ABSTRACT

A multi-layer sheet of collagen membrane material includes a barrier layer including an outer smooth barrier face and further including a fibrous face opposite the smooth barrier face, and a matrix layer of collagen material adhered to the fibrous face, the matrix layer including collagen I, collagen III, or a combination thereof, the matrix layer carrying cultivated bone-forming cells including osteocytes, osteoblasts, stromal cells and/or stem cells committed to differentiation into bone-forming osteoblasts.

6 Claims, 1 Drawing Sheet

Related U.S. Application Data application No. 11/046,897, filed on Feb. 1, 2005, now abandoned, which is a continuation-in-part of application No. 10/213,437, filed on Aug. 7, 2002, now abandoned, said application No. 11/046,897 is a continuation-in-part of application No. 09/925,728, filed on Aug. 10, 2001, now Pat. No. 7,141,072, and a continuation-in-part of application No. 09/545,465, filed on Apr. 7, 2000, now Pat. No. 6,752,834, said application No. 11/046,897 is a continuation-in-part of application No. 10/869,909, filed on Jun. 18, 2004, now abandoned, which is a continuation of application No. 09/545,465, filed on Apr. 7, 2000, now Pat. No. 6,752,834, which is a continuation-in-part of application No. PCT/GB98/02976, filed on Oct. 5, 1998.

(60) Provisional application No. 60/357,839, filed on Feb. 21, 2002, provisional application No. 60/311,078, filed on Aug. 10, 2001, provisional application No. 60/224,010, filed on Aug. 10, 2000.

(51) Int. Cl.
*A61L 31/04* (2006.01)
*A61K 35/12* (2006.01)

(56) References Cited

U.S. PATENT DOCUMENTS

| | | | |
|---|---|---|---|
| 4,880,429 | A | 11/1989 | Stone |
| 4,975,527 | A | 12/1990 | Koezuka et al. |
| 5,162,430 | A | 11/1992 | Rhee et al. |
| 5,167,961 | A | 12/1992 | Lussi et al. |
| 5,197,985 | A | 3/1993 | Caplan et al. |
| 5,206,023 | A | 4/1993 | Hunziker |
| 5,254,133 | A | 10/1993 | Seid |
| 5,413,597 | A | 5/1995 | Krajicek |
| 5,417,975 | A | 5/1995 | Lussi et al. |
| 5,523,348 | A | 6/1996 | Rhee et al. |
| 5,541,295 | A | 7/1996 | Barrach et al. |
| 5,567,806 | A | 10/1996 | Abdul-Malak et al. |
| 5,573,771 | A | 11/1996 | Geistlich et al. |
| 5,624,463 | A | 4/1997 | Stone et al. |
| 5,759,190 | A | 6/1998 | Vibe-Hansen et al. |
| 5,763,416 | A | 6/1998 | Bonadio et al. |
| 5,837,278 | A * | 11/1998 | Geistlich et al. ............ 424/444 |
| 5,989,269 | A | 11/1999 | Vibe-Hansen et al. |
| 6,120,514 | A | 9/2000 | Vibe-Hansen et al. |
| 6,153,292 | A | 11/2000 | Bell et al. |
| 6,165,785 | A * | 12/2000 | Ogle et al. ................ 435/347 |
| 6,221,109 | B1 * | 4/2001 | Geistlich et al. ........... 623/17.11 |
| 6,283,980 | B1 | 9/2001 | Vibe-Hansen et al. |
| 6,352,558 | B1 * | 3/2002 | Spector ................... 623/18.11 |
| 6,576,015 | B2 * | 6/2003 | Geistlich et al. ........... 623/16.11 |
| 6,713,085 | B2 * | 3/2004 | Geistlich et al. ............ 424/443 |
| 6,752,834 | B2 * | 6/2004 | Geistlich et al. ........... 623/23.63 |
| 6,863,900 | B2 * | 3/2005 | Kadiyala et al. ............ 424/426 |
| 7,141,072 | B2 * | 11/2006 | Geistlich et al. ........... 623/23.74 |
| 2001/0016772 | A1 | 8/2001 | Lee et al. |

FOREIGN PATENT DOCUMENTS

| | | |
|---|---|---|
| DE | 38 10803 A1 | 10/1989 |
| DE | 196 54 884A A1 | 9/1997 |
| EP | 0171176 A2 | 2/1986 |
| FR | 2679778 | 2/1993 |
| JP | 2033388 | 2/1990 |
| JP | 4-501070 A | 2/1992 |
| JP | 8-510984 A | 11/1996 |
| JP | 2001-333974 | 4/2001 |
| WO | WO 83/04177 A1 | 12/1983 |
| WO | 90/01955 A1 | 3/1990 |
| WO | WO 90/05755 A1 | 5/1990 |
| WO | WO 90/13302 A1 | 11/1990 |
| WO | WO 92/13565 A1 | 8/1992 |
| WO | WO 93/10722 A2 | 6/1993 |
| WO | WO 93/11723 A1 | 6/1993 |
| WO | WO 93/19168 A1 | 9/1993 |
| WO | 94/21556 A1 | 9/1994 |
| WO | WO 95/18638 A1 | 7/1995 |
| WO | WO 96/24310 A1 | 8/1996 |
| WO | WO 96/25961 A1 | 8/1996 |
| WO | WO 97/32616 A1 | 9/1997 |
| WO | WO 98/02976 A1 | 1/1998 |
| WO | WO 98/08469 A2 | 3/1998 |
| WO | WO 99/11664 A1 | 3/1999 |
| WO | WO 99/19005 A1 | 4/1999 |
| WO | WO 01/08714 A1 | 2/2001 |
| WO | WO 01/15711 A1 | 3/2001 |
| WO | WO 01/24842 A2 | 4/2001 |
| WO | WO 01/91816 A1 | 12/2001 |

OTHER PUBLICATIONS

H.A. Breinan et al., "Reparative Tissues in Articular Cartilage Defects in a Canne Model Treated by Microfracture", 45th Annual Meeting, Orthopaedic Research Society, Feb. 1-4, 1999, Anaheim, CA. (one page).

C.R. Lee et al., "Harvest and Selected Cartilage Repair Procedures Affect Mechanical and Biochemical Properties of Uninvolved Articular Cartilage in the Canine Knee", 45th Annual Meeting, Orthopaedic Research Society, Feb. 1-4, 1999, Anaheim, CA. (one page).

C.R. Lee et al., "The Contractile Behavior of Articular Chondrocytes in Collagen Matrices In Vitro", Tissue Engineering Soc., Dec. 4-6, 1998, Orlando, Fla. (one page).

S.M. Mueller et al., "Alpha-Smooth Muscle Actin in Bovine Meniscus Cells Seeded in Type I and Type II Collagen-GAG Matrices", 44th Annual Meeting, Orthopaedic Research Society, Mar. 16-19, 1998, New Orleans, Louisiana. (one page).

S. Nehrer et al., "Chondrocyte-Seeded Type I and Type II Collagen Implants Investigated In Vitro", Fifth World Biomaterials Congress, May 29-Jun. 2, 1996, Toronto, CA. (one page).

S. Nehrer et al., "Autologous Chondrocyte-Seeded Type I and II Collagen Matrices Implanted in a Chondral Defect in a Canine Model", 44th Annual Meeting, Orthopaedic Research Society, Mar. 16-19, 1998, New Orleans, Louisiana. (one page).

S. Nehrer et al., "Chondrocyte-Seeded Type I and Type II Collagen Matrices Implanted in a Chondral Defect in a Canine Model", 7th Conference European Orthopaedic Research Society, Barcelona, 1997. (one page).

S. Nehrer et al., "Characteristics of Articular Chondrocytes Seeded in Collagen Matrices In Vitro", Tissue Engineering, 1998, pp. 175-183, vol. 4(2).

S. Nehrer et al., "Matrix Collagen Type and Pore Size Influence Behaviour of Seeded Canine Chondrocytes", Biomaterials 18, (1997), pp. 769-776.

Donna Schulz-Torres et al., "Tendon Cell Contraction of Collagen-GAG Matrices In Vitro: Effect of Cross-Linking", Soc. for Biomaterials, Apr. 28-May 2, 1999, Providence, R.I. (one page).

S. Nehrer et al., "Canine Chondrocytes Seeded in Type I and Type II Collagen Implants Investigated In Vitro", J. Biomed. Mater. Res. (Appl. Biomater.), 1997, pp. 95-104, vol. 38, John Wiley & Sons, Inc.

"Carticel (Autologous cultured chondrocytes): Get in the Game", *Genzyme Tissue Repair*, 9 pp., 1998.

Menard, C., et al., "Contractile behavior of smooth muscle actin-containing osteoblasts in collagen-GAG matrices in vitro: implant-related cell contraction", *Biomaterials*, 21 (2000) 1867-1877.

Database WPI, 002241043, Derwent Publications Ltd., Jul. 26, 1990.
Database WPI, 002241044, Derwent Publications Ltd., Dec. 4, 2001.
Database Biosis, 002242287, "Lapine and canine bone marrow stromal cells contain smooth muscle actin and contract a collagen-slycoasminoglycan matrix", Dec. 2001.

Pieper, J.S., et al., "Development of Tailor-made Collagen-glycosaminoglycan Matrices: EDC/NHS Crosslinking, and Ultrastructural Aspects", *Biomaterials*, vol. 21, pp. 581-593 (2000).

(56) References Cited

OTHER PUBLICATIONS

Stone, K., et al., "Regeneration of Meniscal Cartilage with Use of a Collagen Scaffold", *The Journal of Bone and Joint Surgery, Incorporated*, vol. 79-A, No. 12, 1997, pp. 1770-1777.

S.M. Mueller et al., "α-Smooth Muscle Actin and Contractile Behavior of Bovine Meniscus Cells Seeded in Type I and Type II Collagen-GAG Matrices", J. Biomed. Mat. Res., 1999, pp. 1-10, vol. 45, John Wiley & Sons, Inc.

Genzyme Tissue Repair, "Carticel™ (autologous cultured chondrocytes), Engineering a Better Repair", Genzyme Tissue Repair, 64 Sidney Street, Cambridge, MA 02139-4136, Sep. 1997, brochure. (8 pages).

D. Mutter et al., "Biomaterial Supports for Colonic Wall Defect Healing", Biomaterials 17, 1996, pp. 1411-1415.

T.O. Schneider et al.: "Expression of α-Smooth Muscle Actin in Canine Intervertebral Disc Cells In Situ and in Collagen-Glycosaminoglycan Matrices In Vitro," Journal of Orthopaedic Research, vol. 17, 192-199, 1999.

Office Action issued in Canadian Patent Appln. No. 2,419,620 on Nov. 22, 2012, 4 pages.

Office Action issued in Japanse Patent Appln. No. 2009-264245 on Dec. 25, 2012 along with English translation, 5 pages.

"Iwanami Seibutsugaku Jiten (Biological Dictionary) the Fourth Edition", Iwanami Shote, Publishers, Nov. 10, 1998, p. 1029, left column "Cartilage Tissue", along with English translation, 4 pages.

* cited by examiner

CELL-CHARGED MULTI-LAYER COLLAGEN MEMBRANE

CROSS-REFERENCE TO RELATED APPLICATIONS

This application is a continuation-in-part of U.S. application Ser. No. 11/317,247, filed Dec. 27, 2005, which is a continuation-in-part of U.S. application Ser. No. 10/367,979, filed Feb. 19, 2003 now abandoned, which claims benefit of U.S. Provisional Application No. 60/357,839, filed Feb. 21, 2002. The present application also is a continuation-in-part of U.S. application Ser. No. 11/046,897, filed Feb. 1, 2005 now abandoned, which is a continuation-in-part of U.S. application Ser. No. 10/213,437, filed Aug. 7, 2002 now abandoned, which claims the benefit of U.S. Provisional Application Ser. No. 60/311,078, filed Aug. 10, 2001. U.S. application Ser. No. 11/046,897 also is a continuation-in-part of U.S. application Ser. No. 09/925,728, filed Aug. 10, 2001 (now U.S. Pat. No. 7,141,072), which claims the benefit of U.S. Provisional Application Ser. No. 60/224,010 filed Aug. 10, 2000. U.S. application Ser. No. 09/925,728 also is a continuation-in-part of U.S. application Ser. No. 09/545,465, filed Apr. 7, 2000 (now U.S. Pat. No. 6,752,834). U.S. application Ser. No. 11/046,897, also is a continuation-in-part of U.S. application Ser. No. 10/869,909, filed Jun. 18, 2004 now abandoned, which is a continuation of U.S. application Ser. No. 09/545,465, filed Apr. 7, 2000, now U.S. Pat. No. 6,752,834. U.S. application Ser. No. 09/545,465 is a continuation-in-part of International Application Ser. No. PCT/GB98/02976, filed Oct. 5, 1998.

FIELD OF THE INVENTION

The present invention relates to the field of reconstruction of bone tissue.

DESCRIPTION OF THE BACKGROUND ART

There remains a need in the art for materials and methods for promoting regeneration and reconstruction of bone tissue such as in the maxilla and other skeletal bone loss defects.

SUMMARY OF THE INVENTION

A multi-layer sheet of collagen membrane material comprising a barrier layer including an outer smooth barrier face and further including a fibrous face opposite said smooth barrier face, and a matrix layer of collagen material adhered to said fibrous face, the matrix layer comprising collagen I, collagen III, or a combination thereof, said matrix layer carrying cultivated bone-forming cells including at lest one of osteocytes, osteoblasts, stromal cells or stem cells committed to differentiation into bone-forming osteoblasts.

DETAILED DESCRIPTION OF THE INVENTION

The present invention provides a method for reconstruction of bone. In preferred embodiments, a method for reconstruction of bone includes the steps of covering the area to be treated with a patch comprising a sheet of collagen membrane material, wherein the collagen membrane material comprises a barrier layer having a smooth face and a fibrous face opposite the smooth face, the fibrous face allowing cell growth thereon, wherein the collagen membrane further comprises a matrix layer comprising collagen I, collagen III, or a combination thereof carrying cultivated bone-forming cells selected from the group consisting of osteocytes, osteoblasts, stromal stem cells, and stem cells committed to differentiation into bone-forming osteoblasts. In preferred embodiments, the barrier layer is predominantly or consists essentially of collagen I, collagen III or a combination thereof. In preferred embodiments the matrix layer also is predominantly or consists essentially of collagen I, collagen III or a combination thereof. In preferred embodiments, the sheet of collagen membrane material consists essentially of the barrier and the matrix layers, carrying cells and optionally other bone growth-stimulating or cartilage growth-stimulating agents according to the invention.

The present invention has unexpected advantages, including that the matrix layer is absorbed by the body at a faster rate than the barrier layer, leaving the barrier layer to protect the site for an extended period while healing is promoted by the cells of the matrix.

Collagen occurs in a number of forms in the animal body, and different tissues contain different proportions of the respective types. Collagen sponge material used in medicine and in cosmetics is generally derived from skin and tendons, and is comprised predominantly of collagen I and/or collagen III. Bone collagen comprises predominantly collagen I and collagen III.

Figure 1:
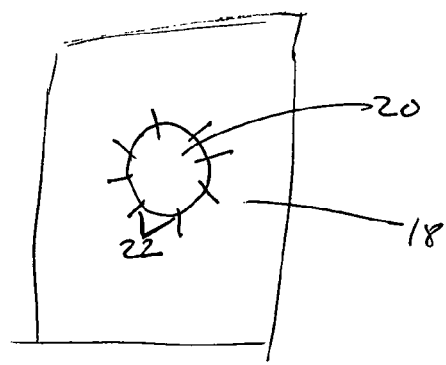
FIG. 1 is a schematic plan view showing a patch of collagen membrane covering an area of bone loss with to be treated in accordance with one embodiment of the present invention.

FIG. 1 shows a defect on a bone 18 repaired by placing a membrane 20 over the defect and securing the patch around the defect. The patched area is then allowed to regenerate the bone tissue. In FIG. 1, the membrane 20 may be held in place by any suitable means, such as adhesive or fasteners 22.

Figure 2:
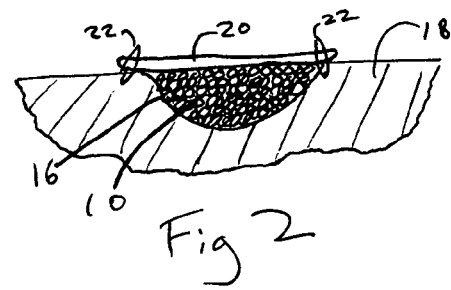
FIG. 2 is a schematic view in partial cross section of an area of bone loss being treated in accordance with another embodiment of the present invention.

FIG. 2 shows a bone loss defect 16 in bone 18 which may be in the maxilla, or other skeletal bone. In the embodiment shown in FIG. 2, porous bone mineral matrix material 10, which carries bone-forming cells in accordance with the present invention, is packed into the bone defect 16. The bone mineral matrix packing 10 may be held in place by a membrane 20 by any suitable means, such as adhesive or fasteners 22. In certain embodiments, membrane 20 is a collagen matrix carrying bone-forming cells in accordance with the present invention. In another embodiment, the bone defect is covered with a collagen matrix 20 carrying bone-forming cells in accordance with the present invention, without the addition of bone mineral matrix 10.

Figure 3:
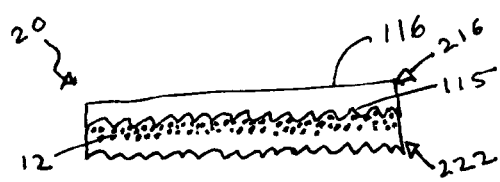
FIG. 3 is a side elevation schematic view showing a membrane carrying bone-forming cells in accordance to one embodiment of the present invention.

FIG. 3 shows a multi-layer collagen membrane 20 that can be used as a patch in accordance with the present invention. This membrane includes a first collagen barrier layer 216, and further includes a second collagen matrix layer 222. The second collagen layer 222 is adhered to the fibrous face 115 of the first collagen barrier layer 216 for placement against the bone surface to promote regeneration of bone. The second matrix layer 222 can be formed of collagen I, III, or a combination of these collagen types, but is preferably formed of predominantly collagen I and collagen III (e.g., about 95% Type I collagen and 5% Type III collagen). The matrix layer 222 carries cells 12 as described herein. The combination of the first and second layers 216 and 222 increases the thickness of the membrane 20 for easy handling and improved healing (as noted above). The thickness of the membrane can vary depending upon application but will typically range between about 0.1 mm to about 5 mm. The thickness may range between about 0.5 mm to about 5 mm, or may range between about 2 mm to about 5 mm. Also, a thickness of about 3 mm may be utilized.

In preferred embodiments, the barrier layer 216 is predominantly collagen I, collagen III or a mixture thereof. One suitable material for this layer is Biogide®, from Ed. Geistlich Söhne AG für Chemische Industrie, the assignee of the present invention. The Biogide® material is described in U.S. Pat. No. 5,837,278, incorporated herein by reference.

Preferred embodiments include a collagen I/III barrier layer (e.g., Bioguide® membrane) and a collagen I/III matrix layer formed of milled collagen I/III (e.g., by milled Bioguide®). The milled material may be applied as a slurry to the barrier layer and then freeze dried to adhere it to the barrier layer. Alternatively, the milled slurry can be formed into a freeze dried matrix sheet and later adhered to the fibrous face of the collagen I and/or III barrier layer by adhesive, e.g., non-sutured adhesive.

The barrier and matrix layers may be formed from any suitable material, such as bovine or porcine material, and preferably is formed from porcine material, most preferably porcine membrane.

As noted above, the barrier and matrix layers may be connected to one another, or combined, in any suitable manner. Examples of suitable methods of combination include: attaching the matrix layer to the fibrous face of the barrier layer with fibrin glue; attaching the matrix layer to the fibrous face of the barrier layer using collagen slurry; or coating the fibrous face of the barrier layer with a collagen slurry of the desired collagen type for the matrix membrane layer, and then freeze-drying the combination.

If desired, growth factors such as EGF (Epidermal Growth Factor), IGF-1 (Insulin-like Growth Factor), β-FGF (Fibroblast Growth Factor), PDGF (Platelet-derived Growth Factor), TGF-β (Transforming Growth Factor) which promote bone regeneration, can be charged to the matrix, and/or added to the surface of the matrix that is placed against the bone.

To aid in regenerating bone tissue, the matrix is impregnated with osteocytes, osteoblasts, stromal stem cells (e.g., present in bone marrow) or osteoblast-forming stem cells, either prior to or following implantation in vivo. While the matrix may be impregnated with the cells immediately prior to implantation, e.g. by injection, the cells may be introduced into the matrix by direct injection of a suspension of cells following implantation. In this way, the cells present in the matrix are able to facilitate regeneration of new bone.

The cells for use in the invention may be obtained from cell sources which include allogenic or autogenic cells isolated from tissue containing the cells. Since allogenic cells carry the potential for immune response and infectious complications, it is preferable to isolate the cells from autogenic cells. Techniques for harvesting cells are known and include enzymatic digestion or outgrowth culture. The harvested cells are then expanded in cell culture prior to reintroduction to the body.

Alternatively, bone marrow or bone marrow derivatives containing stromal stem cells can be charged into the matrix.

In general, it is desirable for the matrix according to the invention to contain glycosaminoglycans (GAGs) such as hyaluronic acid, chondroitin 6-sulphate, keratin sulphate, dermatan sulphate, etc., which serve to provide a natural medium in which osteoblasts or osteoblast-forming stem cells can become embedded and grow. While it is possible to incorporate into the matrix glycosaminoglycans from different sources which do not necessarily have the same composition, molecular weight and physiological properties as those from cartilage, preferred glycosaminoglycans are those extracted from cartilage itself.

In native collagen tissues GAGs occur, at least in part, as a component of proteoglycans (PGs). The use of GAGs in the form of PGs is undesirable in view of potential immunological problems which can be caused by the protein content of the PGs. Preferably, the matrix is thus substantially free from any proteoglycans. Conveniently, this may be achieved by preparing the matrix from a mixture of a purified telopeptide-free collagen material and glycosaminoglycans.

Other additives which may also be present in the matrix include, for example, chondronectin, laminin, fibronectin, bone and cartilage cell growth-promoting hormones, and growth factors such as cartilage inducing factor (CIP), insulin-like growth factor (IGF), transforming growth factor β (TGFβ) present as homodimers or heterodimers, osteogenic protein-1 (OP-1) and bone morphogenetic factors (BMPs) such as native or recombinant human BMP-2, BMP-3 (osteogenin), BMP-4, BMP-7, BMP-8, BMP-12, bFGF, CDMP or other skeletal matrix molecules, as well as signaling peptides such as transforming growth factor-β (TGF-β, TGF-β1), vascular endothelial growth factor (EGF/VEGF), insulin-like growth factor (IGF/IGF-1), parathyroid hormone related protein (PTHrP) and platelet derived growth factor (PDGF). Nucleic acid sequences coding for the above, or which are capable of inducing or promoting in vivo production of the above, may be incorporated into the matrix material of the present invention.

As noted above, the product used in the invention also may act as a carrier for stem cells committed to differentiation into bone-producing cells. Such stem cells may be grown in vitro to increase their numbers, and applied to the repair sites in the carrier matrices with or without growth factors. An example is bone marrow stromal cells. Nucleic acid sequences coding for the above, or which are capable of inducing or promoting in vivo production of the above, may be incorporated into the matrix material of the present invention.

BMP-2 affects the two pathways of bone formation independently—the direct formation of bone as well as the formation of cartilage which is then removed and replaced by bone. Composites of BMPs and collagen including bone matrix obtained by extraction from cortical bone from various sources or demineralized bone matrix comprise about 90% collagen and about 10% non-collagenous proteins (NCP) for BMP activity or for BMP/NCP induced chondrogenesis. Bone matrix-insoluble collagenous matrix and laminin or fibronectin act as carriers for BMPs. In general, the matrix may contain from about 100 μg to about 5 mg of growth factors. Nucleic acid sequences coding for the above, or which are capable of inducing or promoting in vivo production of the above, may be incorporated into the matrix material of the present invention.

A matrix material for use in accordance with the present invention may also be charged with parathyroid hormone (PTH), a polypeptide involved in regulation of calcium in the body. Nucleic acid sequences coding for the above, or which are capable of inducing or promoting in vivo production of the above, may be incorporated into the matrix material of the present invention.

As noted above, the present invention may comprise a gene or nucleic acid-charged matrix with cell growth-promoting genetic material or DNA incorporated therein. The matrix material may provide for prolonged release of the cell growth-promoting genetic material. Upon release from the matrix into the body, the genetic material may transform cells in the body so as to promote cell growth and healing.

The present invention may also provide a matrix material charged with a cell growth-promoting nucleic acid sequence, preferably an isolated or purified nucleic acid sequence. The sequence can be a DNA sequence or an RNA sequence. In particularly preferred embodiments, the matrix material is charged with an isolated gene sequence, most preferably of DNA.

A nucleic acid sequence for use in accordance with the present invention may promote bone cell growth, cartilage cell growth or both.

Purified therapeutic nucleic acid sequences for use in accordance with the present invention may be derived from any suitable source, and may be charged to the matrix material so as to promote cell growth. In accordance with one embodiment, a retroviral vector, or any other suitable gene-carrying and gene-introducing mechanism, is utilized. For example, a retroviral vector may be utilized for stably introducing human bone morphogenic protein 7 (BMP-7) cDNA into mesenchymal stem cells.

Gene therapy involves the delivery of therapeutic genes or other genetic material into cells and tissues.

As will be further discussed below, a collagen matrix of the invention may be prepared by forming an aqueous collagen slurry, optional partial dehydration of the slurry, molding the slurry to the desired shape, drying of the slurry, partial cross-linking of the collagen fibers by chemical, ultraviolet (UV) radiation, enzymatic or thermal cross-linking, and sterilizing the implant material. Alternatively, cross-linking, can be effected after preparation of the slurry and prior to or after application of the slurry to the barrier layer.

In preferred embodiments, the matrix material is dried by freeze-drying so as to achieve a pore size within the range of about 0.1-500 µm. A preferred pore size for a matrix in accordance with the invention is within the range of about 50-400 µm, most preferably within the range of about 70-120 µm.

The density of the matrix after freeze-drying preferably is within the range of about 0.1-0.3 g/m$^3$, preferably about 0.18-0.22 g/m$^3$, most preferably about 0.2 g/m$^3$.

Collagen material may be cross-linked before or after the freeze-drying step to stabilize the matrix. This also serves to increase the mechanical stability of the matrix and to reduce its rate of resorption by the body. Ideally, the degree of cross-linking should be such that the rate of degradation of the matrix matches the rate of tissue regeneration.

Physically, cross-linking may be carried out by heating, but this must be effected carefully to avoid undesired loss of resorbability. Heating to temperatures of 100-120° C. for a period of from about 30 minutes to about 5 hours is preferable. More preferably, cross-linking may be effected by UV irradiation using a UV lamp, e.g., for a period of up to 8 hours.

As noted above, the collagen matrix material advantageously contains glycosaminoglycans (GAGs). The latter actually reacts with collagen to effect some cross-linking and produces an insoluble product. If necessary, further cross-linking can be effected by heating the material, by UV irradiation, or by further chemical cross-linking as discussed above. The reaction between the glycosaminoglycans and collagen can be effected at ambient temperatures at a pH in the range 2.5-3.5. The matrix material may be subjected to freezing and freeze-drying immediately after such treatment.

For example, GAGs such as chondroitin sulphate (CS) may be covalently attached to the matrix using 1-ethyl-3-(3-dimethyl aminopropyl) carbodiimide (EDC) and N-hydroxysuccinimide (NHS) utilizing known methods. EDC/NHS crosslinking may be utilized for immobilizing GAGs with matrices, which may include dermatan sulphate, heparin, heparan sulphate, and hyaluronic acid, as well as CS as indicated above.

Slurry formation may be effected by raising the pH of a collagen mass. In this procedure, the mass is cooled to about 4° C. and the pH value slowly raised by addition of cold aqueous NaOH at 4° C. up to a pH value about 6.5-7.5. Subsequently, the mass is held at ambient temperature for about 15-25 hours. In this time, the slurry is formed and after slurry formation, the slurry can be frozen and/or freeze-dried.

A still further alternative is to neutralize a collagen mass to a pH value about 6.8-7.4, subsequent to removal of air. The mixture is incubated for about 15-20 hours at 37° C. A fine slurry develops which can subsequently be frozen and freeze-dried.

After forming the slurry, the material may be frozen. In order to obtain a reproducible pore size, the freezing must be carefully controlled and the rate and time of freezing, the pH value and the particle size must be accurately controlled.

The matrix is then freeze-dried and subsequently heated to about 110-130° C. In this way, some cross-linking is effected. Subsequently, the freeze-dried matrix may be adjusted to the required thickness. The matrix is then sterilized, for example by gamma-irradiation or with ethyleneoxide. Sterilization by strong irradiation e.g. with $^{60}$Co in doses of 25 kGy may deactivate the BMPs. In such circumstances, the sterile matrix may be impregnated with BMPs in sterile saline prior to implantation.

When cross-linking is effected utilizing chemical agents, various aldehydes such as hyaluronate polyaldehyde, formaldehyde or glyoxal may be used. Suitable chemical cross-linking agents include hyaluronate polyaldehyde, hexaethylene di-isocyanate, di-ethyl-3-(3-dimethyl aminopropyl) carbodimide (EDC), and N-hydroxy succinimide (NHS) or a mixture of EDC and NHS.

The membrane for use in accordance with the present invention may be used in conjunction with a porous bone mineral matrix material or a combination of collagen matrix material and porous bone mineral matrix material. A bone mineral containing matrix material utilized in accordance with the present invention may contain any suitable additions as outlined above with respect to collagen matrix materials in accordance with the present invention.

The purified bone mineral may, for example, be a product as described in International Patent Application WO 86/07265 (PCT/GB86/00310). Such products may be prepared by rigorously de-greasing particulate bone, e.g. bovine femurs, and treating with ammonia or an organic amine to degrade residual protein followed by extensive water washing. Such material remains resorbable on implementation, assisting the remodeling process.

It is also possible to prepare purified bone mineral by calcinating particulate cancellous or cortical bone e.g. at 900 C for 24 hours. Such calcined bone mineral is of use where permanent, non-resorbable implants are required, for example in ridge augmentation.

In either way after removal of organic material, the bone is excessively brittle and its strength is greatly improved by treatment according to the invention.

When bone mineral is used with the present invention the bone mineral may provide a substrate for cells to affect bone regeneration.

Commonly owned U.S. Pat. No. 5,573,771 (incorporated herein by reference) discloses a medicinal bone mineral product in which the bone mineral is strengthened by a matrix made up of Type I collagen (collagen I), or a mixture of Type I collagen and Type III collagen (collagen I and collagen III).

The product according to the invention may be used for bone regeneration in maxilla, articulating joints, knees, feet, spine, etc., and with remodeling implants or prosthetic bone replacements, for example in orthopedic surgery including hip revisions, replacement of bone loss, e.g. in traumatology, remodeling in maxillo-facial surgery or filling periodontal defects and tooth extraction sockets, including ridge augmentation.

The invention is applicable to repair of maxilla bone defects, and regeneration of articular joint defects in which both the cartilage and underlying bone is damaged.

To enhance regeneration, cultivated cells utilized with the invention can be added to the bone mineral before implantation, and the charged bone mineral then can be implanted during open surgery or arthroscopic surgery. The implanted can be covered with a cell-charged collagen membrane according to the invention. Such collagen membrane be applied over the filled-in bone implant by open surgery or arthroscopic surgery.

In accordance with one embodiment, the product of the invention comprises at least one absorbed pharmaceutically or biologically active substance or mesenchymal stem cells having an ability to differentiate into cells to regenerate bone, or bone and cartilage.

Physiologically active substances which may be charged to the collagen matrix and the bone mineral may be at least partially water-soluble and include antibacterial substances such as sulphonamides, e.g., condensation products of formaldehyde with taurinamide or N-substituted taurinamide, such as taurolidine, taurultam and mixtures thereof, as well as antibiotics such as penicillins, cephalosporin, aminoglycosides etc.

Other useful physiologically active substances include proteins and polypeptides capable of assisting bone regeneration especially non-collagenous proteins derived from bone matrix and bone cells. These include mitogenic factors such as skeletal growth factor and morphogenic and angiogenic factors as well as transforming bone growth factor. Growth factors from the matrix such as ossein or more preferably osteopoietin are particularly beneficial.

Matrices produced in accordance with the invention are charged with a suspension of osteocytes, osteoblasts, stromal stem cells (e.g., in bone marrow material) or osteoblast-forming stem cells to form a bone healing combination material in accordance with the present invention.

The invention claimed is:

1. A multi-layer sheet of collagen membrane material comprising:
    a barrier layer which consists essentially of collagen I and collagen III, wherein the barrier layer has an outer smooth barrier face and a fibrous face opposite said smooth barrier face; and
    a matrix layer which contains collagen I, collagen III or a combination of collagen I/collagen III, and excludes substantial amounts of collagen II, said matrix layer carrying expanded bone-forming cells in bone marrow material,
    wherein said matrix layer is adhered to said fibrous face of said barrier layer.

2. The multi-layer sheet of claim 1 wherein said membrane material has a thickness of about 0.1-5 mm.

3. The multi-layer sheet of claim 1 wherein said matrix layer further carries at least one bone growth-stimulating agent or cartilage growth-stimulating agent.

4. A method for reconstructing bone tissue, comprising applying the collagen membrane material of claim 1 to a bone defect, wherein the matrix layer is placed in contact with the bone defect, so as to promote reconstruction of bone tissue at said defect.

5. The method of claim 4 wherein said membrane material has a thickness of about 0.1-5 mm.

6. The method of claim 4 wherein said matrix layer further carriers at least one bone growth-stimulating agent or cartilage growth-stimulating agent.

* * * * *